United States Patent [19]

Iso et al.

[11] 4,424,228

[45] Jan. 3, 1984

[54] ANTIHYPERTENSIVE AGENT COMPRISING A THIAZOLIDINE CARBOXYLIC ACID AND PROBENECID

[75] Inventors: Tadashi Iso, Sakai; Hideyasu Yamauchi, Osaka, both of Japan

[73] Assignee: Santen Pharmaceutical Co., Ltd., Osaka, Japan

[21] Appl. No.: 380,664

[22] PCT Filed: Sep. 18, 1981

[86] PCT No.: PCT/JP81/00236

§ 371 Date: May 4, 1982

§ 102(e) Date: May 4, 1982

[87] PCT Pub. No.: WO82/00954

PCT Pub. Date: Apr. 1, 1982

[30] Foreign Application Priority Data

Sep. 20, 1980 [JP] Japan ............................. 55-131348

[51] Int. Cl.$^3$ .......................................... A61K 31/425
[52] U.S. Cl. ................... 424/270; 424/263; 424/267; 424/273 R; 424/274; 424/282; 424/319; 548/201
[58] Field of Search ......................................... 424/270

[56] References Cited

FOREIGN PATENT DOCUMENTS 2018248 10/1979 United Kingdom ............... 424/270

OTHER PUBLICATIONS

Chemical Abstracts, 75:128323y (1971) [Vetter, W., et al., Z. Gesamte Exp. Med., 1971, 155(3), 234–244].

Vtter, W. et al., Z. Gesamte Exp. Med., 1971, 155(3), 234–244.

Osaka-fu Byoin Yakuzaishikai-ken, "Iyakuhin Yoran", pp. 100–101, 8/20/76.

Primary Examiner—Richard A. Schwartz
Attorney, Agent, or Firm—Frishauf, Holtz, Goodman & Woodward

[57] ABSTRACT

This invention relates to an antihypertensive agent comprising N-(mercaptoacyl)amino acid and probenecid.

The concomitant effect of probenecid and N-(mercaptoacyl)amino acid was observed to reduce the effective dose of N-(mercaptoacyl)amino acid and to prolong the duration time of the effect.

8 Claims, 1 Drawing Figure

ANTIHYPERTENSIVE AGENT COMPRISING A THIAZOLIDINE CARBOXYLIC ACID AND PROBENECID

TECHNICAL FIELD

This invention is directed to novel compositions for use as antihypertensive agents.

BACKGROUND OF THE INVENTION

N-(Mercaptoacyl)amino acids, inhibitors against angiotensin I converting enzyme, have been approved as drugs for the treatment of renal hypertension.

On the other hand, probenecid, a drug for the treatment of gout having uricosuric action, has been known to suppress the elimination of some organic acids from renal tubules. To date, this suppressive action of probenecid on the renal secretion has been useful to prolong the duration of drugs, especially, the concomitant use of penicillin and probenecid is known.

Generally, diuretics are used together with antihypertensive drugs. However, there is no report about the concomitant use of inhibitors against angiotensin I converting enzyme and probenecid.

SUMMARY OF THE INVENTION

We investigated the concomitant effect of probenecid and N-(mercaptoacyl)amino acid which reveal antihypertensive effect because of the inhibition against angiotensin I converting enzyme.

The concomitant effect of probenecid was observed to reduce the effective dose of N-(mercaptoacyl)amino acid and prolong the duration of the effect against angiotensin I converting enzyme.

This invention therefore relates to an antihypertensive agent comprising N-(mercaptoacyl)amino acid and probenecid.

DETAILED DESCRIPTION OF THE INVENTION

Figure 1:
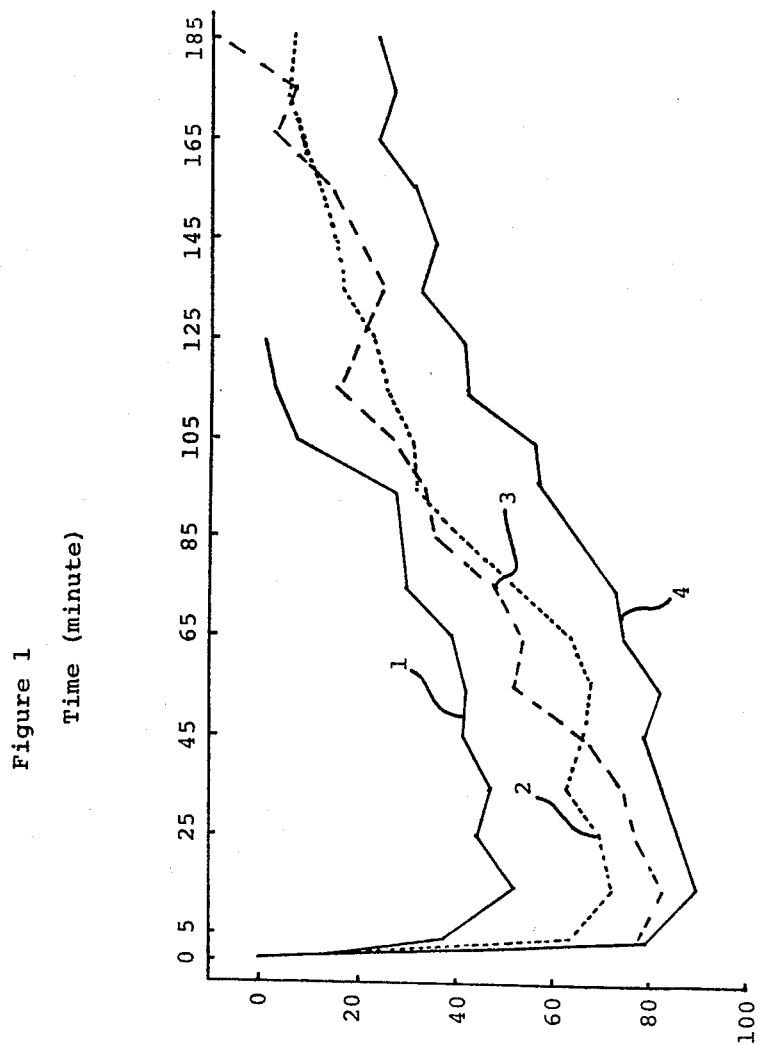

The above-mentioned N-(mercaptoacyl)amino acid is represented by the following formula [I]

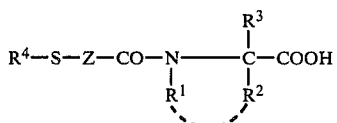

wherein
$R^1$ is hydrogen or lower alkyl;
$R^2$ is hydrogen, lower alkyl, phenyl, aralkyl, imidazolylalkyl or indolyl-alkyl, which may be substituted by lower alkyl, hydroxy, acylhydroxy, methylenedioxy, mercapto, acylmercapto, amino, guanidino or carboxy;
$R^1$ and $R^2$ may join to complete pyrrolidine ring, piperidine ring or thiazolidine ring, and each ring may be substituted by lower alkyl, aralkyl, phenyl, furyl, thienyl, pyridyl or naphthyl, which may be further substituted by lower alkyl, hydroxy-lower alkyl, mercapto-lower alkyl, hydroxy, lower alkoxy, alkylenedioxy, halogen, nitro, amino, lower alkylamino or acylamino;
$R^3$ is hydrogen or methyl;
$R^4$ is hydrogen, acyl or residual group except $R^4$ from the formula [I];
Z is straight or branched alkylene containing 1 to 3 carbon atoms, and salts thereof.

The antihypertensive effect is shown by the following pharmacological test.

Pharmacological Test

N-(mercaptoacyl)amino acid inhibiting angiotensin I converting enzyme can suppress the pressor response to angiotensin I. The concomitant effect of probenecid to N-(mercaptoacyl)amino acid was evaluated pharmacologically by determing the suppressive activity against the blood pressor response to angiotensin I according to the following procedure.

Experimental procedure

Male wistar strain rats weighing 200–300 g were used.

Under ether anesthesia, polyethylene cannulas were inserted into the femoral artery and vein. The cannula to the femoral artery was connected to a pressure transducer apparatus. After complete recovery from anesthesia, 300 ng/Kg of angiotensin I was injected intravenously and the pressure responce was recorded by polygraph(Nihon Koden, RM-6000). Probenecid and N-(mercaptoacyl)amino acid were suspended in 0.5% tragacanth solution, respectively. At 30 minutes after the oral administration of probenecid, 0.5 ml/Kg (1 mg/Kg) of N-(mercaptoacyl)amino acid was administered orally and the pressor response to angiotensin I injected intravenously was measured with time.

The inhibitory effect against angiotensin I converting enzyme was presented as the percentage inhibition of pressor response to angiotensin I.

Experimental result

FIG. 1 shows that 1 mg/Kg of orally administrated (2R,4R)-2-(2-hydroxyphenyl)-3-(3-mercaptopropionyl)-4-thiazolidinecarboxylic acid (compound A), one of N-(mercaptoacyl)amino acids, suppressed the pressor response to angiotensin I.

The concomitant effect of probenecid intensified and the prolonged suppressive effect were produced by the compound A. The concomitant effect of probenecid (1–100 mg/Kg) was found to depend upon the dose of probenecid.

BRIEF EXPLANATION FOR FIGURE

FIG. 1 shows the time course of the suppressive effect of N-(mercaptoacyl)amino acid with or without probenecid.

In the FIGURE, line 1 is the effect produced by 1 mg/Kg of compound A; line 2, by 1 mg/Kg of compound A with 1 mg/Kg of probenecid; line 3, by 1 mg/Kg of compound A with 10 mg/Kg of probenecid; line 4, by 1 mg/Kg of compound A with 100 mg/Kg of probenecid. The vertical axis presents the percentage inhibition of the blood pressor response to angiotensin I.

BEST MODE OF MAKING AND USING THE INVENTION

The concomitant ratio of probenecid can be 1 to 100 mg/Kg against 0.01 to 10 mg/Kg of N-(mercaptoacyl)amino acid.

The combination of drugs can be prepared into tablets, granules, or injection by normal procedures without the special regards because of stability of the both drugs.

UTILITY IN AN INDUSTRIAL FIELD

This invention offers novel compositions of antihypertensive agents useful for medical treatment.

What we claim is:

1. An antihypertensive composition comprising (1) an antihypertensive effective amount of an N-(mercaptoacyl)-amino acid and (2) probenecid, said N-(mercaptoacyl)-amino acid having the formula

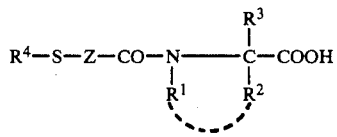

wherein
$R^1$ and $R^2$ join to form a thiazolidine ring substituted with phenyl, or phenyl substituted with a substituent selected from the group consisting of lower alkyl, hydroxy, lower alkoxy, halogen, nitro and amino;
$R^3$ is hydrogen;
$R^4$ is hydrogen; and
Z is a straight or branched alkylene containing 1 to 3 carbon atoms.

2. The antihypertensive composition of claim 1, wherein said N-(mercaptoacyl)-amino acid is present in an amount of at least 0.01 mg/kg.

3. The antihypertensive composition of claim 2, wherein said N-(mercaptoacyl)-amino acid is present in an amount between 0.01 and 10 mg/kg.

4. The antihypertensive composition of claim 1, wherein said probenecid is present in an amount between 1 and 100 mg/kg.

5. The antihypertensive composition of claim 1, wherein the ratio of said probenecid is 1 to 100 mg/kg to 0.01 to 10 mg/kg of said N-(mercaptoacyl)-amino acid.

6. The antihypertensive composition of claim 1 or 3 or 5, wherein said N-(mercaptoacyl)-amino acid is (2R,4R)-2-(2-hydroxyphenyl)-3-(3-mercaptopropionyl)-4-thiazolidinecarboxylic acid.

7. A method of treating hypertension in a warm blooded animal comprising administering to said warm blooded animal the composition of claim 1.

8. A method of treating hypertension in a warm blooded animal comprising administering to said warm blooded animal the composition of claim 5.

* * * * *